(12) United States Patent
Nakada

(10) Patent No.: US 7,110,809 B2
(45) Date of Patent: Sep. 19, 2006

(54) MUSCLE FATIGUE MEASURING EQUIPMENT

(75) Inventor: Masato Nakada, Asaka (JP)

(73) Assignee: Tanita Corporation, Tokyo (JP)

( * ) Notice: Subject to any disclaimer, the term of this patent is extended or adjusted under 35 U.S.C. 154(b) by 514 days.

(21) Appl. No.: 10/620,705

(22) Filed: Jul. 17, 2003

(65) Prior Publication Data

US 2004/0019290 A1    Jan. 29, 2004

(30) Foreign Application Priority Data

Jul. 24, 2002    (JP) ............... 2002-214861

(51) Int. Cl.
*A61B 5/04*    (2006.01)
(52) U.S. Cl. ..................... 600/546; 600/547
(58) Field of Classification Search ............... 600/546, 600/547
See application file for complete search history.

(56) References Cited

U.S. PATENT DOCUMENTS

| | | | | |
|---|---|---|---|---|
| 4,667,513 A | * | 5/1987 | Konno | ............... 73/379.01 |
| 5,349,963 A | | 9/1994 | Eskelinen | |
| 5,645,073 A | * | 7/1997 | Kadefors et al. | ............... 600/546 |
| 5,701,894 A | * | 12/1997 | Cherry et al. | ............... 600/300 |
| 6,181,961 B1 | * | 1/2001 | Prass | ............... 600/547 |
| 6,185,451 B1 | * | 2/2001 | Richardson et al. | ............... 600/546 |
| 6,472,888 B1 | * | 10/2002 | Oguma et al. | ............... 324/691 |
| 2001/0007055 A1 | | 7/2001 | Fukuda | |
| 2001/0020138 A1 | * | 9/2001 | Ishigooka et al. | ............... 600/547 |
| 2002/0156392 A1 | * | 10/2002 | Arai et al. | ............... 600/546 |
| 2004/0082876 A1 | * | 4/2004 | Viertio-Oja et al. | ............... 600/544 |

FOREIGN PATENT DOCUMENTS

| | | |
|---|---|---|
| EP | 1 114 610 | 7/2001 |
| JP | 2000-232 | 1/2000 |
| JP | 2002-224072 | 8/2002 |

\* cited by examiner

*Primary Examiner*—Max F. Hindenburg
*Assistant Examiner*—Helen Nguyen
(74) *Attorney, Agent, or Firm*—McDermott Will & Emery LLP

(57) ABSTRACT

Muscle fatigue measuring equipment is provided by which one can know muscle fatigue status objectively and easily. Embodiments include equipment for performing the steps of substituting a myoelectric value based on a measured myoelectric potential and a stored myoelectric value into an arithmetic expression for determining a myoelectric change; and substituting an extracellular fluid measured using biological impedance and a stored extracellular fluid value into an arithmetic expression for determining a change in extracellular fluid. The presence or absence of muscle fatigue, the equilibrium state of muscle fatigue, and the progress of muscle fatigue is determined using the determined myoelectric change and extracellular fluid change.

15 Claims, 6 Drawing Sheets

MUSCLE FATIGUE MEASURING EQUIPMENT

BACKGROUND OF THE INVENTION (i) Field of the Invention

This invention relates to muscle fatigue measuring equipment for estimating the fatigue status of a muscle.

(ii) Description of the Related Art

It is important for athletes, rehabilitants and others to know the fatigue statues of their muscles so as to build their muscular strengths. For information, the relationship between muscle fatigue and passage of time is represented by a graph shown in FIG. 8, for example. During training, muscle fatigue accumulates and increases (muscular strength lowers) as time elapses, as can be seen in an accumulation period. This occurs due to a breakage of a muscle caused by use of the muscle. Then, after the training, the muscle fatigue lowers (muscular strength recovers) as time elapses, as can be seen in a normal recovery period. This occurs due to physiological restoration of the muscle. Then, as can be seen in a super recovery period, the muscle fatigue continuously lowers as time elapses, and after it becomes slightly lower than pre-training muscle fatigue (muscular strength improves), it restores to the pre-training muscle fatigue. This occurs since the muscular strength improves once by a defense mechanism for adapting to a load given during the training but restores to original muscular strength for adapting to life strength.

Based on the relationship between muscle fatigue and passage of time as shown in FIG. 8, trainees (athletes, rehabilitants and others) have relied on subjective estimations to know what their current muscle fatigue statuses are, i.e., whether their muscle fatigues are in accumulation, in recovery or other statuses.

In other words, trainees (athletes, rehabilitants and others) have not been able to know what their current muscle fatigue statuses are, objectively and easily.

SUMMARY OF THE INVENTION

Thus, an object of the present invention is to solve the above conventional problems and provide muscle fatigue measuring equipment by which one can know a muscle fatigue status objectively and easily.

To achieve the above object, the muscle fatigue measuring equipment of the present invention comprises:

myoelectric change acquiring means, extracellular fluid change acquiring means, and muscle fatigue status determining means, wherein the myoelectric change acquiring means acquires a myoelectric change of a living body, the extracellular fluid change acquiring means acquires a change in extracellular fluid of the living body, and the muscle fatigue status determining means determines a muscle fatigue status from the myoelectric change acquired in the myoelectric change acquiring means and the change in extracellular fluid acquired in the extracellular fluid change acquiring means in accordance with criteria for determining a muscle fatigue status based on a myoelectric change and a change in extracellular fluid.

Further, the myoelectric change acquiring means comprises:

myoelectric potential measuring means, first storage means, and myoelectric change computing means, the myoelectric potential measuring means measures a myoelectric potential occurring along with the movement of a muscle of a living body so as to determine a myoelectric value, the first storage means stores an arithmetic expression for determining a myoelectric change and a myoelectric value at a base time, and the myoelectric change computing means computes a myoelectric change by substituting the myoelectric value determined by the myoelectric potential measuring means and the myoelectric value stored in the first storage means into the arithmetic expression stored in the first storage means, and the extracellular fluid change acquiring means comprises:

biological impedance measuring means, second storage means, and extracellular fluid change computing means, the biological impedance measuring means provides an alternating current to a living body and measures a voltage caused by a biological impedance so as to determine an extracellular fluid, the second storage means stores an arithmetic expression for determining a change in extracellular fluid and an extracellular fluid at a base time, and the extracellular fluid change computing means computes a change in extracellular fluid by substituting the extracellular fluid determined by the biological impedance measuring means and the extracellular fluid stored in the second storage means into the arithmetic expression stored in the second storage means.

Further, the muscle fatigue measuring equipment of the present invention has measuring electrodes serving both as communication ports to detect the myoelectric potential in the myoelectric potential measuring means and as communication ports to detect the voltage caused by the biological impedance in the biological impedance measuring means and which also has a switching device that switches a signal of the myoelectric potential from the measuring electrodes and a signal of the voltage caused by the biological impedance from one to another.

Further, the muscle fatigue status determining means determines a muscle fatigue status by a series of procedural steps, i.e., comparing a myoelectric change acquired by the myoelectric change acquiring means with a reference value for determining whether the myoelectric change is a myoelectric change at a normal time or not so as to determine the presence or absence of muscle fatigue as the muscle fatigue status, comparing a change in extracellular fluid acquired by the extracellular fluid change acquiring means with a reference value for determining whether the change in extracellular fluid is a change in extracellular fluid at a normal time or not so as to determine the equilibrium state of the muscle fatigue as the muscle fatigue status, and comparing the change in extracellular fluid acquired by the extracellular fluid change acquiring means with a reference value for determining whether the change in extracellular fluid is larger or smaller than the change in extracellular fluid acquired last time so as to determine the progress of the muscle fatigue as the muscle fatigue status.

Further, the extracellular fluid is the ratio of an extracellular fluid to intracellular and extracellular fluids.

Further, the extracellular fluid is an interstitial fluid.

Figure 1:
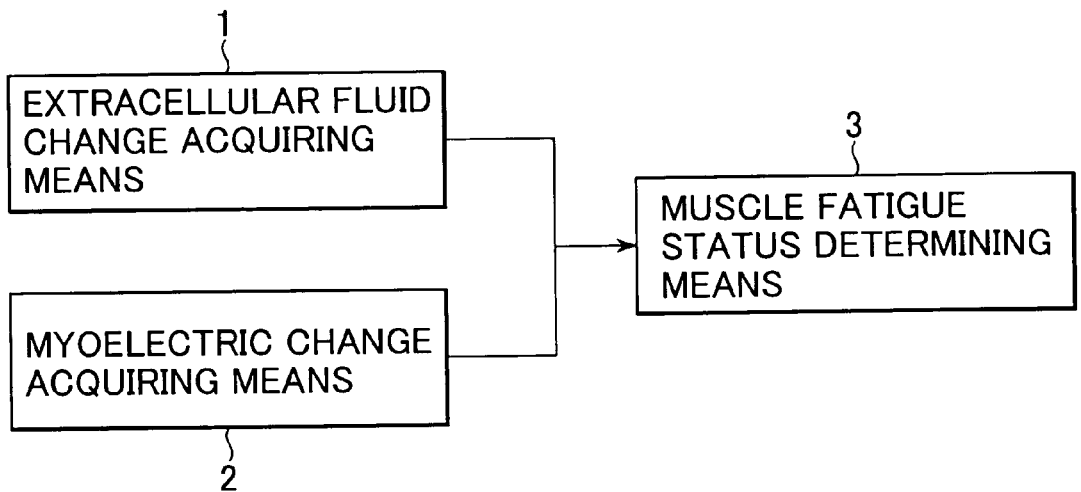
FIG. 1 is a block diagram showing a functional constitution of muscle fatigue measuring equipment.

Reference numeral 1 denotes extracellular fluid change acquiring means; 2 denotes myoelectric change acquiring means; 3 denotes muscle fatigue status determining means; 4 denotes switches; 4a denotes setting switches; 4b denotes individual start switches; 4c denotes a start switch intended solely for measurement of a body weight; 5 denotes a thermometer; 6 denotes a weighing platform; 7 denotes a weight sensor; 8 and 17 denote an amplifier; 9 and 21 denote an A/D converter; 10 denotes body weight computing means; 11 denotes body weight measuring means; 12 denotes constant voltage (sine wave alternating current) generator; 13 and 18 denote a BPF (Band Pass Filter); 14 denotes a V/I converter; 15 denotes current-carrying electrodes; 16 denotes measuring electrodes; 19 denotes an LPF (Low Pass Filter); 20 denotes a switching device; 22 denotes percent body fat computing means; 23 denotes extracellular fluid computing means; 24 denotes myoelectric value computing means; 25 denotes myoelectric change computing means; 26 denotes extracellular fluid change computing means; 27 denotes a microcomputer; 28 denotes a display; 29 denotes biological impedance measuring means; 30 myoelectric potential measuring means; 31 denotes first storage means; 32 denotes second storage means; 33 denotes a ROM; and 34 denotes an EEPROM.

DETAILED DESCRIPTION OF THE PREFERRED EMBODIMENTS

Hereinafter, an embodiment of the present invention will be described with reference to the drawings.

Firstly, the constitution of muscle fatigue measuring equipment according to the present invention will be described with reference to FIG. 1 which is a block diagram showing a functional constitution of the equipment, FIG. 2 which is an oblique perspective view of the appearance of the equipment, and FIG. 3 which is a specific constitution of the equipment.

The muscle fatigue measuring equipment of the present invention comprises, as shown in FIG. 1, extracellular fluid change acquiring means 1, myoelectric change acquiring means 2, and muscle fatigue status determining means 3. The muscle fatigue measuring equipment comprising these means are constituted by specific sections as shown in FIGS. 2 and 3.

Figure 2:
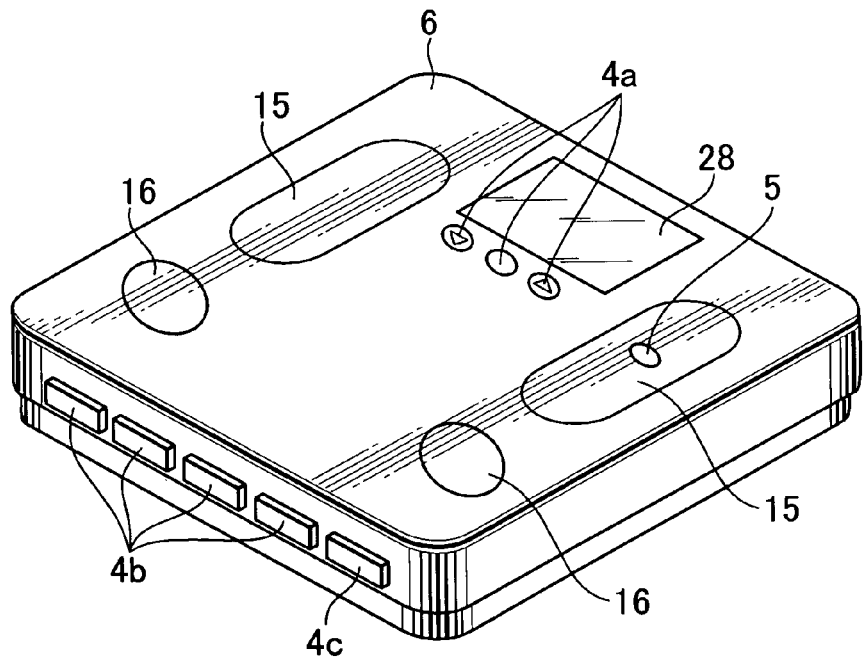
FIG. 2 is an oblique perspective view of the appearance of the muscle fatigue measuring equipment.
Figure 3:
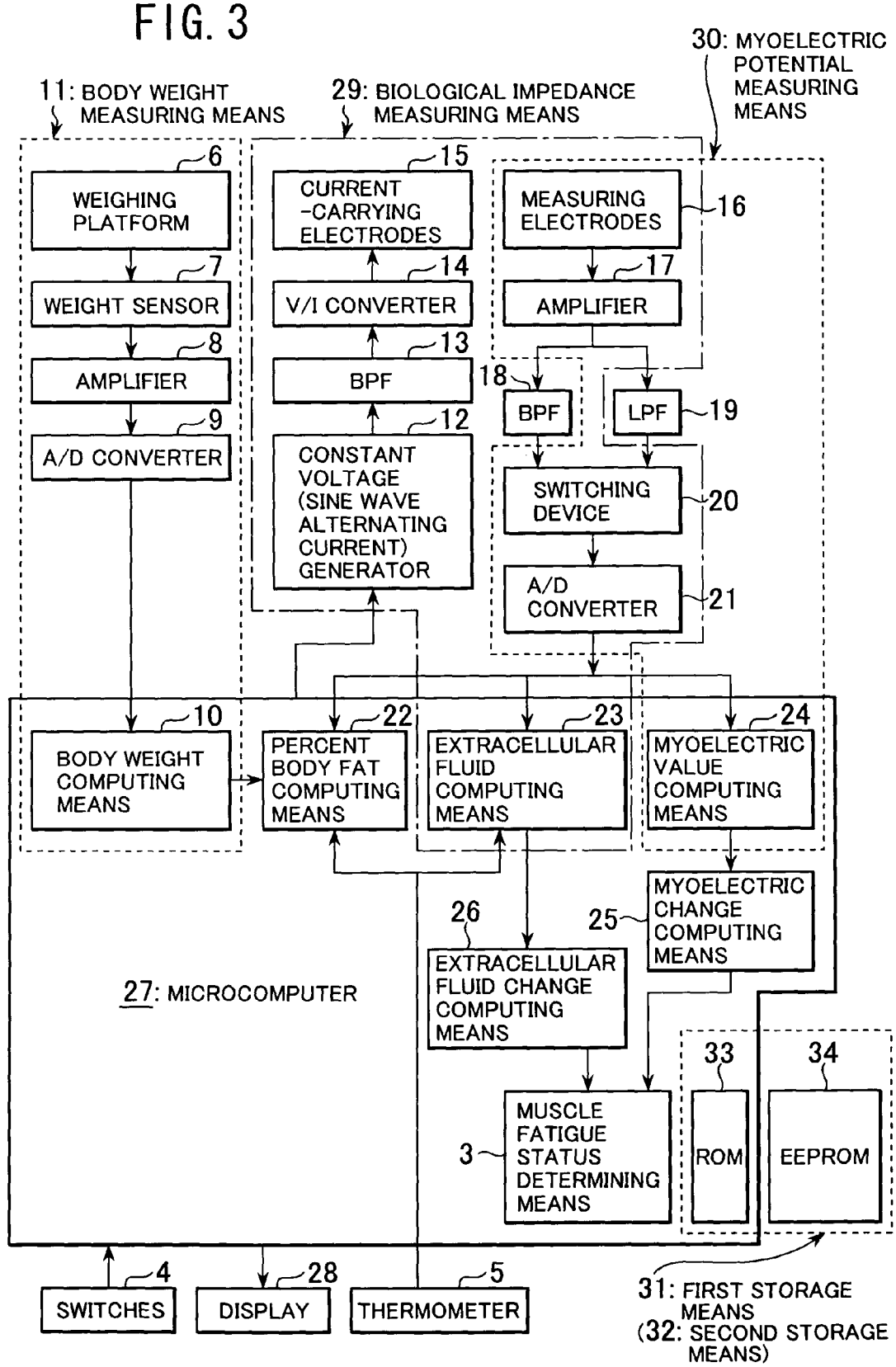
FIG. 3 is a block diagram showing a specific constitution of the muscle fatigue measuring equipment.

Switches 4 shown in FIG. 3 comprise setting switches 4a, individual start switches 4b and a start switch 4c intended solely for measurement of a body weight all of which are shown in FIG. 2. A thermometer 5 is disposed on a weighing platform 6 so as to make contact with the back of a foot, detects the body temperature of a living body and outputs the detected body temperature to percent body fat computing means 22 and extracellular fluid computing means 23 which will be both described later. A microcomputer 27 comprises a known CPU, a ROM 33 and a control unit and performs a variety of computations, data savings and controls to be described later. A display 28 displays a variety of results to be described later and the statuses of inputs by the switches 4.

Body weight measuring means 11 comprises a weighing platform 6, a weight sensor 7, an amplifier 8, an A/D converter 9, body weight computing means 10 and other units found in a known scale and measures a body weight. As in a known percent body fat meter, the percent body fat computing means 22 computes a percent body fat from a voltage caused by a biological impedance when a specific frequency (e.g., 50 kHz) out of a number of frequencies is measured in biological impedance measuring means 29 to be described later. At this point, based on the body temperature of a living body outputted from the foregoing thermometer 5, correction computation of a voltage caused by a biological impedance varying according to changes in the body temperature of the living body is also performed.

The myoelectric change acquiring means 2 acquires a myoelectric change of a living body. The myoelectric change acquiring means 2 comprises myoelectric potential measuring means 30 for measuring a myoelectric potential occurring along with the movement of a muscle of a living body so as to determine a myoelectric value, first storage means 31 for storing an arithmetic expression for determining a myoelectric change and a myoelectric value at a normal time (base time), and myoelectric change computing means 25 for computing a myoelectric change by substituting the myoelectric value determined by the myoelectric potential measuring means 30 and the myoelectric value stored in the first storage means 31 into the arithmetic expression stored in the first storage means 31.

The myoelectric potential measuring means 30 comprises measuring electrodes 16, an amplifier 17, an LPF (Low Pass Filter) 19, a switching device 20, an A/D converter 21 and myoelectric value computing means 24. The measuring electrodes 16 serve as communication ports to detect a voltage caused by the expansion and contraction of a muscle. The amplifier 17 amplifies the voltage detected by the measuring electrodes 16. The LPF 19 allows only a low frequency component of the voltage amplified by the amplifier 17 to pass therethrough. The A/D converter 21 digitizes the low frequency component which has passed through the LPF 19 and sends the digitized voltage to the myoelectric value computing means 24. The myoelectric value computing means 24 computes a myoelectric value v in a known manner from the digitized voltage received from the A/D converter 21. The switching device 20 switches between the LPF 19 and a BPF 18 to be described later.

The first storage means 31 comprises the ROM 33 incorporated in the microcomputer 27 and an EEPROM 34 provided outside the microcomputer 27. The ROM 33 stores an arithmetic expression ($\Delta v = v - vAvg$) for determining a myoelectric change $\Delta v$ in advance. The EEPROM 34 stores a myoelectric value at a normal time (base time) vAvg.

The myoelectric change computing means 25 computes the myoelectric change $\Delta v$ by substituting the myoelectric value v computed by the myoelectric value computing means 24 and the myoelectric value vAvg stored in the EEPROM 34 into the arithmetic expression (Δv=v−vAvg) stored in the ROM 33.

The extracellular fluid change acquiring means 1 acquires a change in extracellular fluid of a living body. The extracellular fluid refers to an extracellular fluid itself, the ratio of an extracellular fluid to intracellular and extracellular fluids or others associated with the extracellular fluid (the same holds true in the following descriptions unless otherwise stated). The extracellular fluid change acquiring means 1 comprises biological impedance measuring means 29 for determining an extracellular fluid by providing alternating currents of different frequencies to a living body and measuring a voltage caused by a biological impedance at each of the frequencies, second storage means 32 for storing an arithmetic expression for determining a change in extracellular fluid and an extracellular fluid at a normal time (base time), and extracellular fluid change computing means 26 for computing a change in extracellular fluid by substituting the extracellular fluid determined by the biological impedance measuring means 29 and the extracellular fluid stored in the second storage means 32 into the arithmetic expression stored in the second storage means 32.

The biological impedance measuring means 29 comprises a constant voltage (sine wave alternating current) generator 12, a BPF (Band Pass Filter) 13, a V/I converter 14, current-carrying electrodes 15, measuring electrodes 16, an amplifier 17, a BPF (Band Pass Filter) 18, a switching device 20, an A/D converter 21 and extracellular fluid computing means 23. The constant voltage (sine wave alternating current) generator 12 generates constant voltages of different frequencies (such as 5 kHz, 50 kHz and 500 kHz). The BPF 13 allows only the frequency components of the constant voltages generated from the constant voltage (sine wave alternating current) generator 12 to pass therethrough. The V/I converter 14 converts the constant voltages received from the BPF 13 to constant currents and outputs the constant currents to the current-carrying electrodes 15. The current-carrying electrodes 15 serve as communication ports to pass the constant currents outputted from the V/I converter 14 through a living body. The measuring electrodes 16 serve as communication ports to detect voltages caused by biological impedances. The amplifier 17 amplifies the voltages detected by the measuring electrodes 16. The BPF 18 allows only specific frequency components (5 kHz, 50 kHz and 500 kHz) of the voltages amplified by the amplifier 17 to pass therethrough. The A/D converter 21 digitizes the voltages which have passed through the BPF 18 and outputs the digitized voltages to the extracellular fluid computing means 23. The extracellular fluid computing means 23 calculates an intracellular fluid Ri and an extracellular fluid (extracellular fluid itself) Re from the digitized voltages (voltages at different frequencies) received from the A/D converter 21 based on the known Cole-Cole circular arc law and further calculates the ratio e of the extracellular fluid (extracellular fluid itself) to the intracellular and extracellular fluids based on an arithmetic expression (e=Re/(Ri+Re)). Further, at this point, the extracellular fluid computing means 23 also performs correction computations of voltages caused by biological impedances varying according to changes in the body temperature of the living body based on the body temperature of a living body outputted from the thermometer 5. The switching device 20 switches between the LPF 19 and the BPF 18. The biological impedance measuring means 29 and the myoelectric potential measuring means 30 share the measuring electrodes 16, the amplifier 17, the switching device 20 and the A/D converter 21.

The second storage means 32 comprises the ROM 33 incorporated in the microcomputer 27 and the EEPROM 34 provided outside the microcomputer 27. The second storage means 32 shares the ROM 33 and the EEPROM 34 with the myoelectric change acquiring means 2. The ROM 33 stores an arithmetic expression (Δe=e−eAvg) for determining a change in extracellular fluid Δe in advance. The EEPROM 34 stores an extracellular fluid at a normal time (base time) eAvg.

The extracellular fluid change computing means 26 computes a change in extracellular fluid Δe by substituting the extracellular fluid e computed by the extracellular fluid computing means 23 and the extracellular fluid eAvg stored in the EEPROM 34 into the arithmetic expression (Δe=e−eAvg) stored in the ROM 33.

The muscle fatigue status determining means 3 determines muscle fatigue from the myoelectric change acquired by the myoelectric change acquiring means 2 and the change in extracellular fluid acquired by the extracellular fluid change acquiring means 1 in accordance with criteria for determining muscle fatigue based on a myoelectric change and a change in extracellular fluid.

Figure 7:
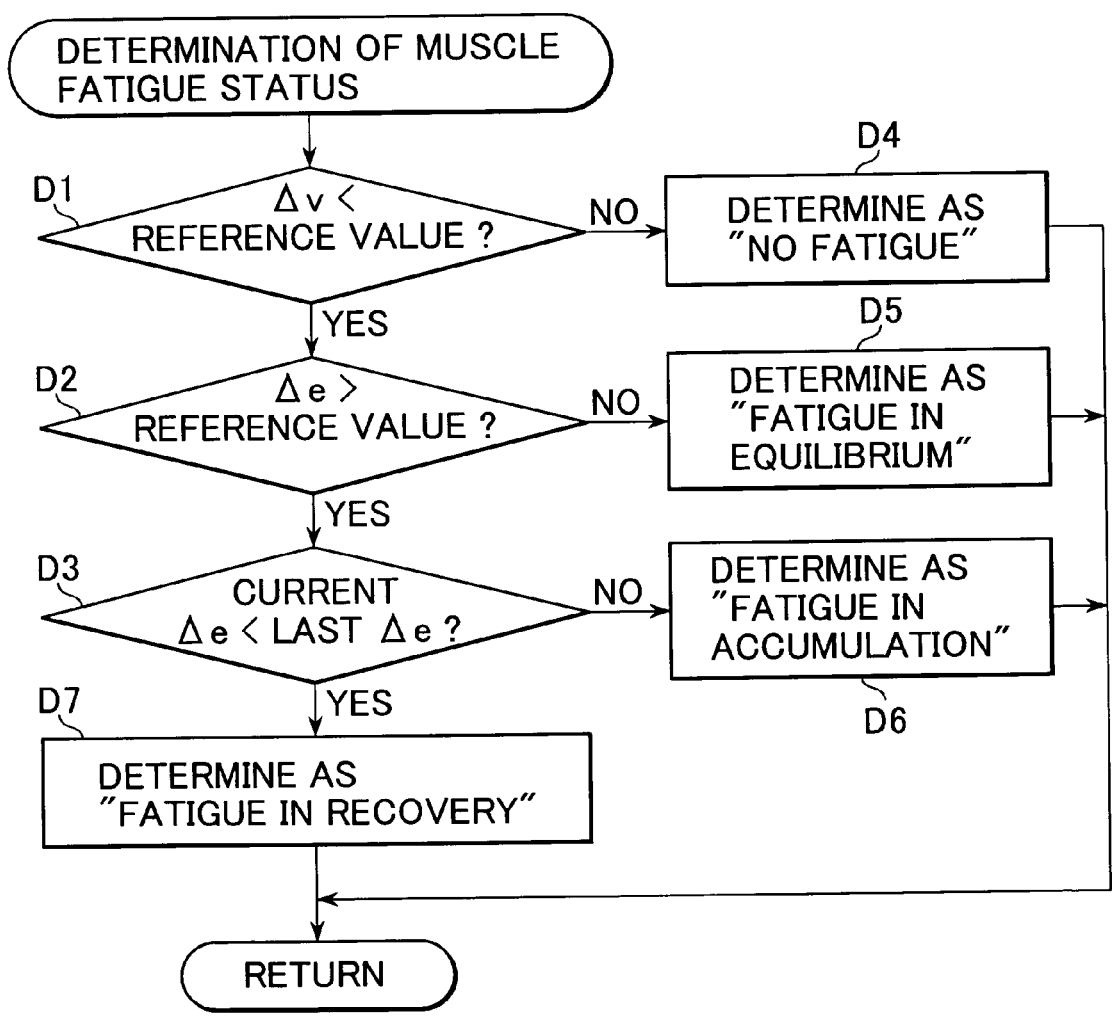
FIG. 7 is a subroutine flowchart showing steps in determination of a muscle fatigue status.
Figure 8:
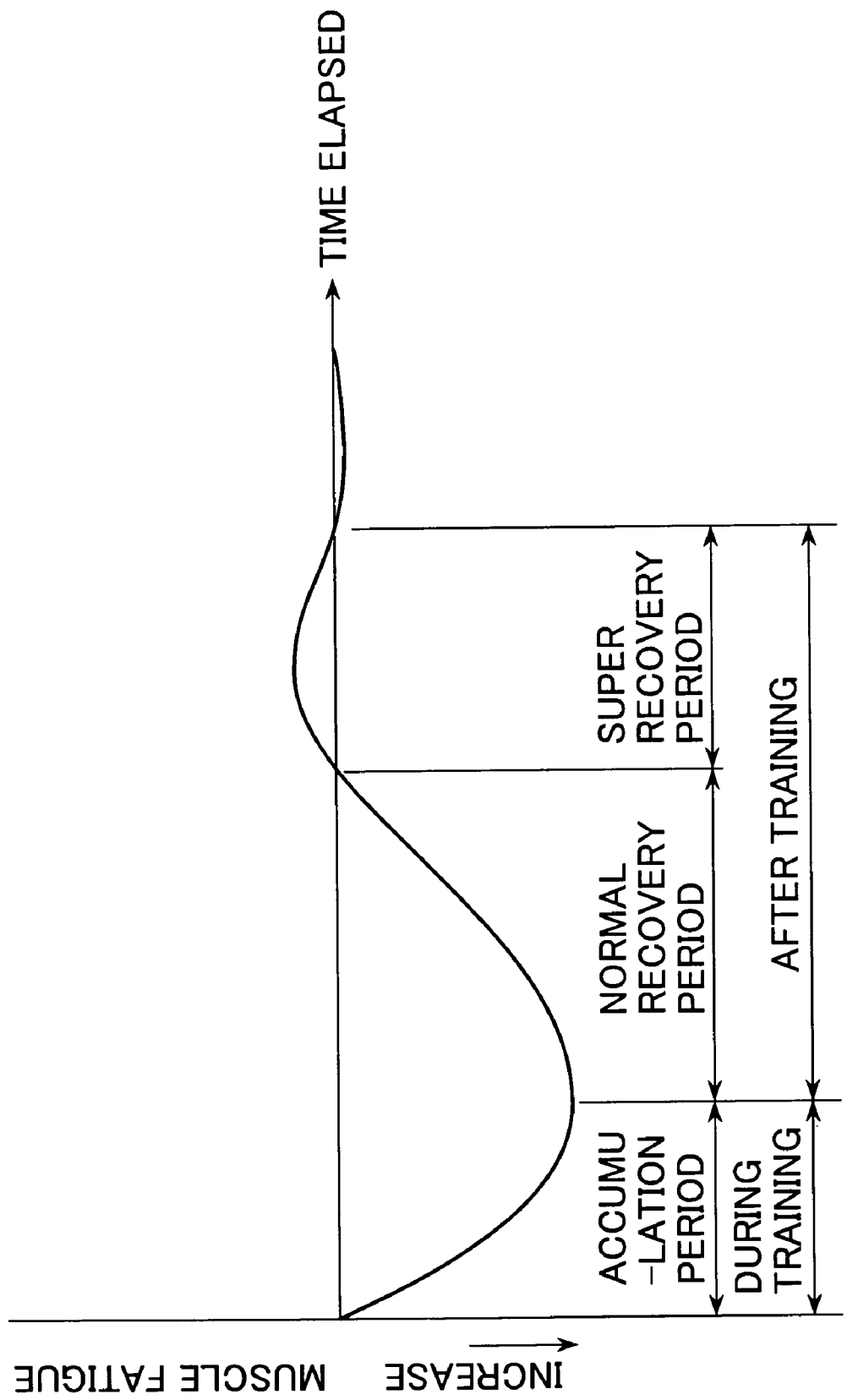
FIG. 8 is a graph illustrating the relationship between muscle fatigue and passage of time.

More specifically, the muscle fatigue status determining means 3 determines a muscle fatigue status by a series of operations indicated by STEP D1 to STEP D7 of a subroutine flowchart for determining muscle fatigue in FIG. 7. That is, the muscle fatigue status determining means 3 determines the muscle fatigue status by a series of operations, i.e., comparing a myoelectric change Δv acquired by the myoelectric change acquiring means 2 with a reference value for determining whether the myoelectric change is a myoelectric change at a normal time or not so as to determine the presence or absence of muscle fatigue as the muscle fatigue status, comparing a change in extracellular fluid Δe acquired by the extracellular fluid change acquiring means 1 with a reference value for determining whether the change in extracellular fluid is a change in extracellular fluid at a normal time or not so as to determine the equilibrium state of the muscle fatigue as the muscle fatigue status, and comparing the change in extracellular fluid Δe acquired by the extracellular fluid change acquiring means 1 with a reference value for determining whether the change in extracellular fluid Δe is larger or smaller than the change in extracellular fluid Δe acquired the last time so as to determine the progress of the muscle fatigue as the muscle fatigue status.

Figure 4:
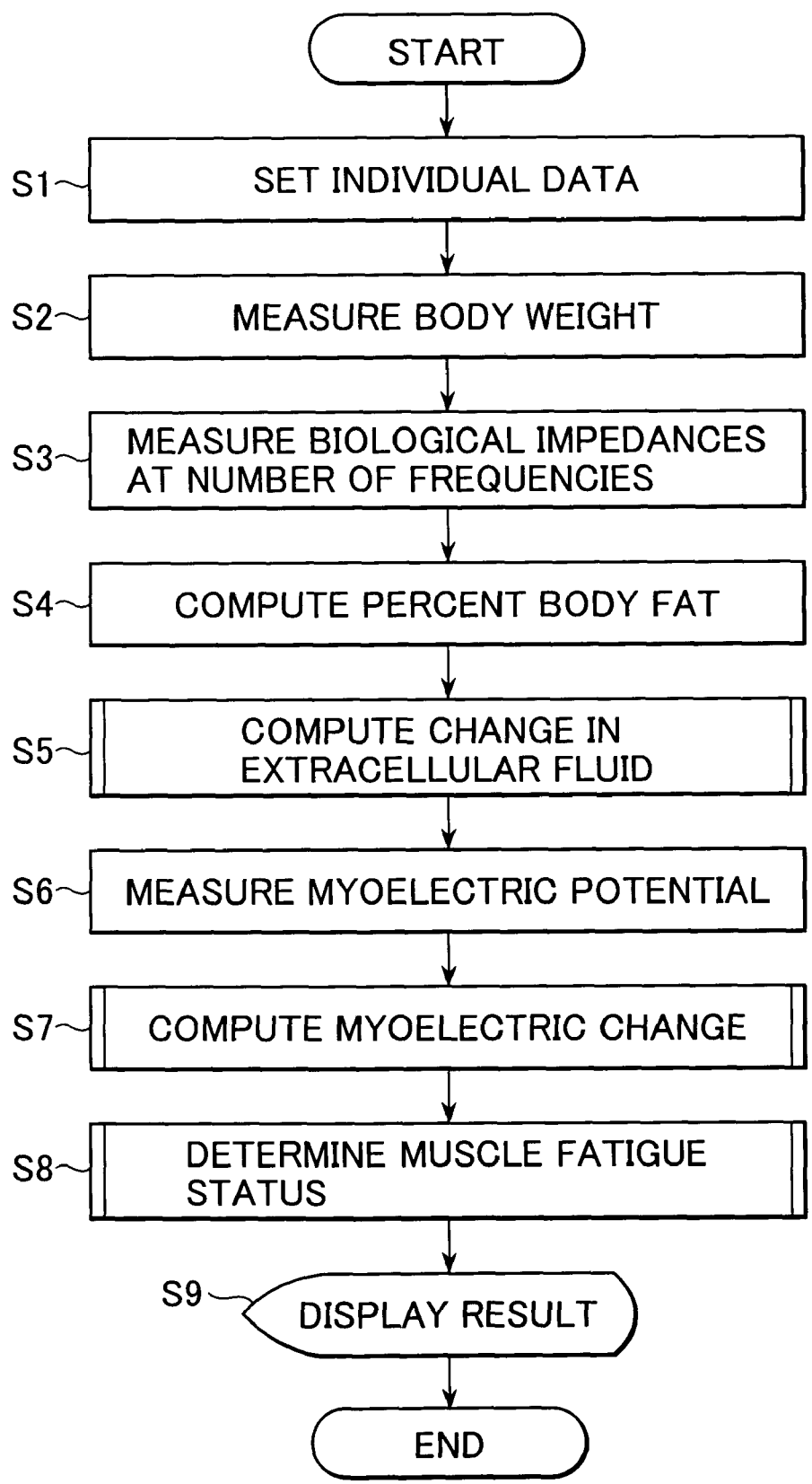
FIG. 4 is a flowchart showing flows of operating procedures and operations of the muscle fatigue measuring equipment.

Next, the operating procedures and operations of the muscle fatigue measuring equipment according to the present invention will be described with reference to a flowchart illustrating flows of operating procedures and operations in FIG. 4.

Firstly, when individual data including physical characteristics of a subject (living body) to be measured is inputted by operating a known device (such as a body fat meter equipped with a scale) by means of the setting switches 4a, the individual data is allocated to an individual start switch 4b in a known manner (STEP S1).

Then, the subject to be measured presses the individual start switch 4b and stands on the weighing platform 6 (in such a manner that the backs of his feet make contact with the current-carrying electrodes 15, measuring electrodes 16 and thermometer 5) upon which his weight is measured by the body weight measuring means 11 in a known manner (STEP S2).

Subsequently, voltages caused by the biological impedances of the subject at a plurality of frequencies are measured by the biological impedance measuring means 29 so as to determine an extracellular fluid (STEP S3).

More specifically, at the press of the individual start switch 4b, the switching device 20 is switched to the BPF 18 side. Then, firstly, a constant voltage of 5 kHz is generated from the constant voltage (sine wave alternating current) generator 12 under the control of the microcomputer 27. Then, only the constant voltage of 5 kHz is allowed to pass through the BPF 13 by the BPF 13. Then, the constant voltage is converted to a constant current by the V/I converter 14, and the constant current is outputted to the current-carrying electrodes 15. Then, the constant current is passed through the subject from the current-carrying electrodes 15, and a voltage caused by the biological impedance of the subject at that time is detected by the measuring electrodes 16. Then, the detected voltage is amplified by the amplifier 17. Then, the BPF 18 allows only a 5 kHz component of the voltage to pass therethrough. Then, the voltage is digitized by the A/D converter 21 and taken in the microcomputer 27. Thereafter, likewise, constant voltages of 50 kHz and 500 kHz are generated from the constant voltage (sine wave alternating current) generator 12 under the control of the microcomputer 27, and voltages caused by biological impedances at that time are taken in the microcomputer 27. Then, an output produced by the body temperature of the living body from the thermometer 5 is taken in the microcomputer 27. Then, in the extracellular fluid computing means 23, an extracellular fluid (extracellular fluid itself) Re and an intracellular fluid Ri are computed from the voltages of 5, 50 and 500 kHz which have been taken in the microcomputer 27 above based on the known Cole-Cole circular arc law. Then, according to the output produced by the body temperature of the living body, the extracellular fluid (extracellular fluid itself) Re and the intracellular fluid Ri are corrected. Further, the ratio e of the extracellular fluid (extracellular fluid itself) to the intracellular and extracellular fluids is calculated based on the arithmetic expression (e=Re/(Ri+Re)).

Subsequently, in the percent body fat computing means 22, a percent body fat is computed from the voltage of 50 kHz which has been taken in the microcomputer 27 as in a known body fat meter (STEP S4).

Thereafter, in the extracellular fluid change computing means 26, a change in extracellular fluid $\Delta e$ is computed by use of the calculated ratio e of the extracellular fluid (extracellular fluid itself) to the intracellular and extracellular fluids (STEP S5).

Figure 5:
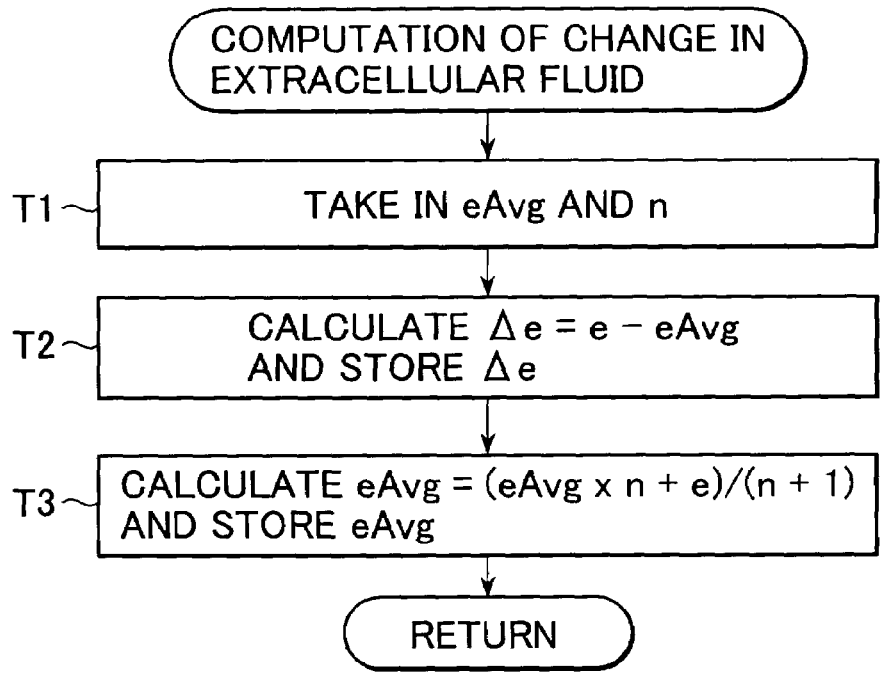
FIG. 5 is a subroutine flowchart showing steps in computation of a change in extracellular fluid.

More specifically, steps as shown in a subroutine flowchart of computation of a change in extracellular fluid in FIG. 5 are carried out. Firstly, the extracellular fluid at a normal time (base time) eAvg which is stored in the EEPROM 34 and the number of measurements n counted by the same individual start switch 4b as used in the above measurement are taken in (STEP T1). Then, the extracellular fluid at a normal time (base time) eAvg and the ratio e of the extracellular fluid (extracellular fluid itself) to the intracellular and extracellular fluids are substituted into the arithmetic expression $\Delta e = e - eAvg$ so as to calculate a change in extracellular fluid $\Delta e$, and the change in extracellular fluid $\Delta e$ is stored in the EEPROM 34 (STEP T2). Then, the extracellular fluid at a normal time (base time) eAvg, the ratio e of the extracellular fluid (extracellular fluid itself) to the intracellular and extracellular fluids and the number of measurements n are substituted into an arithmetic expression eAvg=(eAvg×n+e)/(n+1), and the newly calculated eAvg is stored in the EEPROM 34. Thus, at that time, the original eAvg is updated (STEP T3). Upon completion of STEPS T1 to T3, the subroutine is completed.

Then, a myoelectric potential is measured by the myoelectric potential measuring means 30 so as to determine a myoelectric value v (STEP S6).

More specifically, the switching device is switched to the LPF 19 side. Then, firstly, a voltage (myoelectric potential) occurring along with the movement of a muscle of the living body is detected by the measuring electrodes 16. Then, the detected voltage is amplified by the amplifier 17. Then, the LPF 19 allows only a low frequency component of the voltage to pass therethrough. Then, the voltage is digitized by the A/D converter 21 and then taken in the microcomputer 27. Then, in the myoelectric value computing means 24, the low frequency voltage taken in the microcomputer 27 is squared. Then, after the procedure starting with detection of the voltage by the measuring electrodes 16 and ended with squaring the voltage by the myoelectric value computing means 24 is repeated over e certain time period, the squared myoelectric potentials are averaged so as to determine a myoelectric value v in the myoelectric value computing means 24.

Subsequently, in the myoelectric change computing means 25, a myoelectric change $\Delta v$ is calculated by use of the myoelectric value v calculated in the myoelectric value computing means 24 (STEP S7).

Figure 6:
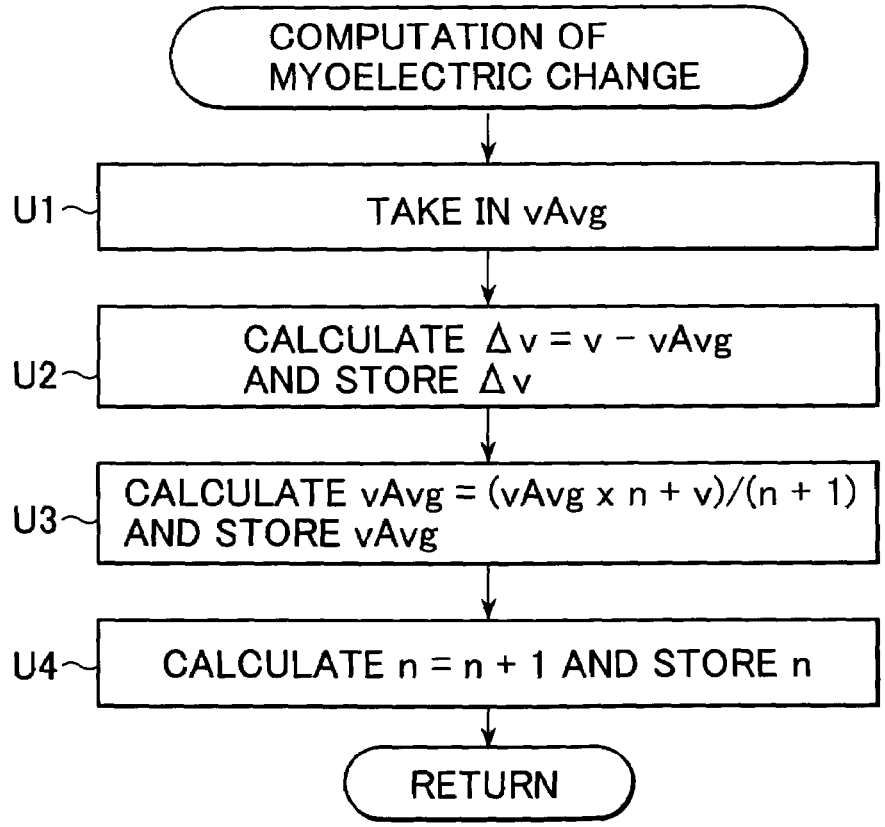
FIG. 6 is a subroutine flowchart showing steps in computation of a myoelectric change.

More specifically, steps as shown in a subroutine flowchart of computation of a myoelectric change in FIG. 6 are carried out. Firstly, the myoelectric value at a normal time (base time) vAvg which is stored in the EEPROM 34 is taken in (STEP U1). Then, based on the myoelectric value vAvg and the myoelectric value v calculated in the myoelectric value computing means 24, a myoelectric change $\Delta v$ is calculated from the expression $\Delta v = v - vAvg$ and then stored in the EEPROM 34 (STEP U2). Then, based on the myoelectric value v calculated in the myoelectric value computing means 24, the myoelectric average value vAvg taken in in STEP U1 and the number of measurements n taken in in STEP T1, a new myoelectric average value vAvg is calculated from an expression vAvg=(vAvg×n +v)/(n+1) and stored in the EEPROM 34. At that time, the original vAvg is updated (STEP U3). Then, the number of measurements n by the individual start switch 4b which has been taken in in STEP T1 is incremented by 1 based on an expression n=n+1, and the new number of measurements n is stored in the EEPROM. At that time, the original n is updated (STEP U4). Upon completion of the above STEPS U1 to U4, the subroutine is completed.

Subsequently, in the muscle fatigue status determining means 3, based on the change in extracellular fluid $\Delta e$ calculated in STEP T3 and the myoelectric change $\Delta v$ calculated in STEP U2, a muscle fatigue status is determined (STEP S8).

More specifically, steps as shown in a subroutine flowchart of determination of a muscle fatigue status in FIG. 7 are carried out. Firstly, the myoelectric change $\Delta v$ stored in the EEPROM 34 and the reference value for a myoelectric change which is programmed in the ROM 33 are compared with each other so as to determine whether they satisfy a relationship "myoelectric change $\Delta v$ <reference value for myoelectric change" (STEP D1). If the relationship "myoelectric change $\Delta v$ <reference value for myoelectric change" is not satisfied (NO in STEP D1), the muscle fatigue status of the subject is determined as "no fatigue" (STEP D4), and the subroutine is terminated.

If the relationship "myoelectric change Δv<reference value for myoelectric change" is satisfied (YES in STEP D1), it is determined whether a relationship "change in extracellular fluid Δe>reference value for change in extracellular fluid" is satisfied (STEP D2). If the relationship "change in extracellular fluid Δe>reference value for change in extracellular fluid" is not satisfied (NO in STEP D2), the muscle fatigue status of the subject is determined as "fatigue in equilibrium" (STEP D5), and the subroutine is terminated.

If the relationship "change in extracellular fluid Δe>reference value for change in extracellular fluid" is satisfied (YES in STEP D2), it is determined whether a relationship "present change in extracellular fluid Δe<last change in extracellular fluid Δe" is satisfied (STEP D3). If the relationship "present change in extracellular fluid Δe<last change in extracellular fluid Δe" is not satisfied (NO in STEP D3), the muscle fatigue status of the subject is determined as "fatigue in accumulation" (STEP D6), and the subroutine is terminated.

If the relationship "present change in extracellular fluid Δe<last change in extracellular fluid Δe" is satisfied (YES in STEP D3), the muscle fatigue status of the subject is determined as "fatigue in recovery" (STEP D7), and the subroutine is terminated.

Then, the status "no fatigue" determined in STEP D4, "fatigue in equilibrium" determined in STEP D5, "fatigue in accumulation" determined in STEP D6 or "fatigue in recovery" determined in STEP D7 is displayed on the display 28 (STEP S9), whereby a series of procedural steps are completed.

As described above, the muscle fatigue measuring equipment of the present invention acquires a myoelectric change of a living body in the myoelectric change acquiring means 2 by measuring a myoelectric potential occurring along with the movement of a muscle of the living body by the myoelectric potential measuring means 30 so as to determine a myoelectric value, storing an arithmetic expression for determining a myoelectric change and a myoelectric value at a normal time (base time) in the first storage means 31, and substituting the myoelectric value measured by the myoelectric potential measuring means 30 and the myoelectric value at a normal time (base time) which is stored in the first storage means 31 into the arithmetic expression stored in the first storage means 31 so as to compute the myoelectric change in the myoelectric change computing means 25.

Meanwhile, a change in extracellular fluid of the living body is acquired in the extracellular fluid change acquiring means 1 by providing alternating currents of different frequencies to the living body and measuring voltages caused by biological impedances at the different frequencies by the biological impedance measuring means 29 so as to determine an extracellular fluid, storing an arithmetic expression for determining a change in extracellular fluid and an extracellular fluid at a base time in the second storage means 32, and substituting the extracellular fluid measured by the biological impedance measuring means 29 and the extracellular fluid at a normal time (base time) which is stored in the second storage means 32 into the arithmetic expression stored in the second storage means 32 so as to compute the change in extracellular fluid in the extracellular fluid change computing means 26.

Then, in the muscle fatigue status determining means 3, a muscle fatigue status is determined by a series of operations, i.e., comparing the myoelectric change acquired by the myoelectric change acquiring means 2 with a reference value for determining whether the myoelectric change is a myoelectric change at a normal time or not so as to determine the presence or absence of muscle fatigue as the muscle fatigue status, comparing the change in extracellular fluid acquired by the extracellular fluid change acquiring means 1 with a reference value for determining whether the change in extracellular fluid is a change in extracellular fluid at a normal time or not so as to determine the equilibrium state of the muscle fatigue as the muscle fatigue status, and then comparing the change in extracellular fluid acquired by the extracellular fluid change acquiring means 1 with a reference value for determining whether the change in extracellular fluid is larger or smaller than the change in extracellular fluid acquired last time so as to determine the progress of the muscle fatigue as the muscle fatigue status.

Thereby, the subject (living body) can know what his current muscle fatigue status is, i.e., whether his muscle fatigue is in equilibrium, in accumulation or in recovery, objectively and easily.

Further, the measuring electrodes 16 are used both as communication ports to detect a myoelectric potential in the myoelectric potential measuring means 30 and as communication ports to detect voltages caused by biological impedances in the biological impedance measuring means 29. A signal of a myoelectric potential from the measuring electrodes 16 and a signal of a voltage caused by a biological impedance are switched from one to another by the switching device. Thereby, measurements can be made by an inexpensive configuration.

In the foregoing embodiment, the myoelectric change acquiring means 2 and the extracellular fluid change acquiring means 1 acquire a myoelectric change and a change in extracellular fluid through measurements. Alternatively, these means may acquire the data through inputting by means of switches.

Further, in the biological impedance measuring means 29, voltages caused by biological impedances of a subject at a plurality of frequencies are measured so as to determine an extracellular fluid. Alternatively, it is also possible that a voltage caused by a biological impedance of a subject is separated into a voltage caused by a resistance component and a voltage caused by a reactance component and an extracellular fluid is determined from the relationship between the voltage caused by the resistance component and the voltage caused by the reactance component.

Further, in the extracellular fluid change acquiring means 1, an extracellular fluid is determined in the biological impedance measuring means 29, a change in extracellular fluid is determined in the extracellular fluid change computing means 26, and in the muscle fatigue status determining means 3, a muscle fatigue status is determined based on the change in extracellular fluid. Alternatively, it is also possible that in the extracellular fluid change acquiring means 1, an interstitial fluid constituting a portion of an extracellular fluid is determined in the biological impedance measuring means 29, a change in the interstitial fluid is determined in the extracellular fluid change computing means 26, and a muscle fatigue status is determined based on the change in interstitial fluid in the muscle fatigue status determining means 3. By determining a muscle fatigue status based on a change in interstitial fluid which is strongly related to muscle fatigue out of changes in extracellular fluid, the degree of reliability of determination is increased.

Further, in the myoelectric potential measuring means, a myoelectric value v is determined by squaring a myoelectric potential. Alternatively, it is also possible that a value which quantitatively represents the movement of a muscle is determined based on ARV (Average Rectified Value)/MPF (Mean Power Frequency) and a myoelectric potential. ARV is a value representing data on the amplitude of a myoelectric value, and MPF is a value representing data on the frequency of the myoelectric value.

As described above, the muscle fatigue measuring equipment of the present invention determines a muscle fatigue status by the muscle fatigue status determining means based on a myoelectric change and a change in extracellular fluid which are acquired by the myoelectric change acquiring means and the extracellular fluid change acquiring means. Thus, a subject to be measured can know his muscle fatigue status objectively and easily.

Further, the myoelectric change acquiring means acquires a myoelectric change through measurements involving the myoelectric potential measuring means, the first storage means and the myoelectric change computing means, and the extracellular fluid change acquiring means acquires a change in extracellular fluid through measurements involving the biological impedance measuring means, the second storage means and the extracellular fluid change computing means. Thus, a subject to be measured can know his muscle fatigue status easily.

Further, the same measuring electrodes are used both as communication ports to detect a myoelectric potential and as communication ports to detect voltages caused by biological impedances, and a signal of a myoelectric potential from the measuring electrodes and a signal of a voltage caused by a biological impedance are switched from one to another by the switching device. Thereby, measurements can be made by an inexpensive configuration.

Further, the muscle fatigue status determining means determines a muscle fatigue status by a series of procedural steps including determination of the presence or absence of muscle fatigue, determination of the equilibrium state of muscle fatigue and determination of the progress of muscle fatigue. Thus, a subject to be measured can know his muscle fatigue status objectively, clearly and easily.

What is claimed is:

1. Muscle fatigue measuring equipment comprising:
   myoelectric change acquiring means,
   extracellular fluid change acquiring means, and
   muscle fatigue status determining means,
   wherein the myoelectric change acquiring means acquires a myoelectric change of a living body,
   the extracellular fluid change acquiring means acquires a change in extracellular fluid of the living body, and
   the muscle fatigue status determining means determines a muscle fatigue status from the myoelectric change acquired in the myoelectric change acquiring means and the change in extracellular fluid acquired in the extracellular fluid change acquiring means in accordance with criteria for determining a muscle fatigue status based on a myoelectric change and a change in extracellular fluid,
   wherein the myoelectric change acquiring means comprises:
   myoelectric potential measuring means,
   first storage means, and
   myoelectric change computing means,
   the myoelectric potential measuring means measures a myoelectric potential occurring along with the movement of a muscle of a living body so as to determine a myoelectric value, the first storage means stores an arithmetic expression for determining a myoelectric change and a myoelectric value at a base time, and
   the myoelectric change computing means computes a myoelectric change by substituting the myoelectric value determined by the myoelectric potential measuring means and the myoelectric value stored in the first storage means into the arithmetic expression stored in the first storage means, and
   the extracellular fluid change acquiring means comprises:
   biological impedance measuring means,
   second storage means, and
   extracellular fluid change computing means,
   the biological impedance measuring means provides an alternating current to a living body and measures a voltage caused by a biological impedance so as to determine an extracellular fluid,
   the second storage means stores an arithmetic expression for determining a change in extracellular fluid and an extracellular fluid at a base time, and
   the extracellular fluid change computing means computes a change in extracellular fluid by substituting the extracellular fluid determined by the biological impedance measuring means and the extracellular fluid stored in the second storage means into the arithmetic expression stored in the second storage means.

2. The equipment of claim 1, which has measuring electrodes serving both as communication ports to detect the myoelectric potential in the myoelectric potential measuring means and as communication ports to detect the voltage caused by the biological impedance in the biological impedance measuring means and which also has a switching device that switches a signal of the myoelectric potential from the measuring electrodes and a signal of the voltage caused by the biological impedance from one to another.

3. The equipment of claim 2, wherein the muscle fatigue status determining means determines a muscle fatigue status by a series of procedural steps, i.e., comparing a myoelectric change acquired by the myoelectric change acquiring means with a reference value for determining whether the myoelectric change is a myoelectric change at a normal time or not so as to determine the presence or absence of muscle fatigue as the muscle fatigue status, comparing a change in extracellular fluid acquired by the extracellular fluid change acquiring means with a reference value for determining whether the change in extracellular fluid is a change in extracellular fluid at a normal time or not so as to determine the equilibrium state of the muscle fatigue as the muscle fatigue status, and comparing the change in extracellular fluid acquired by the extracellular fluid change acquiring means with a reference value for determining whether the change in extracellular fluid is larger or smaller than the change in extracellular fluid acquired last time so as to determine the progress of the muscle fatigue as the muscle fatigue status.

4. The equipment of claim 3, wherein the extracellular fluid is the ratio of an extracellular fluid to intracellular and extracellular fluids.

5. The equipment of claim 3, wherein the extracellular fluid is an interstitial fluid.

6. The equipment of claim 2, wherein the extracellular fluid is the ratio of an extracellular fluid to intracellular and extracellular fluids.

7. The equipment of claim 2, wherein the extracellular fluid is an interstitial fluid.

8. The equipment of claim 1, wherein the muscle fatigue status determining means determines a muscle fatigue status by a series of procedural steps, i.e., comparing a myoelectric change acquired by the myoelectric change acquiring means with a reference value for determining whether the myoelectric change is a myoelectric change at a normal time or not so as to determine the presence or absence of muscle fatigue as the muscle fatigue status, comparing a change in extracellular fluid acquired by the extracellular fluid change acquiring means with a reference value for determining whether the change in extracellular fluid is a change in extracellular fluid at a normal time or not so as to determine the equilibrium state of the muscle fatigue as the muscle fatigue status, and comparing the change in extracellular fluid acquired by the extracellular fluid change acquiring means with a reference value for determining whether the change in extracellular fluid is larger or smaller than the change in extracellular fluid acquired last time so as to determine the progress of the muscle fatigue as the muscle fatigue status.

9. The equipment of claim 8, wherein the extracellular fluid is the ratio of an extracellular fluid to intracellular and extracellular fluids.

10. The equipment of claim 8, wherein the extracellular fluid is an interstitial fluid.

11. The equipment of claim 1, wherein the extracellular fluid is the ratio of an extracellular fluid to intracellular and extracellular fluids.

12. The equipment of claim 1, wherein the extracellular fluid is an interstitial fluid.

13. Muscle fatigue measuring equipment comprising:
myoelectric change acquiring means,
extracellular fluid change acquiring means, and
muscle fatigue status determining means,
wherein the myoelectric change acquiring means acquires a myoelectric change of a living body,
the extracellular fluid change acquiring means acquires a change in extracellular fluid of the living body, and
the muscle fatigue status determining means determines a muscle fatigue status from the myoelectric change acquired in the myoelectric change acquiring means and the change in extracellular fluid acquired in the extracellular fluid change acquiring means in accordance with criteria for determining a muscle fatigue status based on a myoelectric change and a change in extracellular fluid,
wherein the muscle fatigue status determining means determines a muscle fatigue status by a series of procedural steps including comparing a myoelectric change acquired by the myoelectric change acquiring means with a reference value for determining whether the myoelectric change is a myoelectric change at a normal time or not so as to determine the presence or absence of muscle fatigue as the muscle fatigue status, comparing a change in extracellular fluid acquired by the extracellular fluid change acquiring means with a reference value for determining whether the change in extracellular fluid is a change in extracellular fluid at a normal time or not so as to determine the equilibrium state of the muscle fatigue as the muscle fatigue status, and comparing the change in extracellular fluid acquired by the extracellular fluid change acquiring means with a reference value for determining whether the change in extracellular fluid is larger or smaller than the change in extracellular fluid acquired last time so as to determine the progress of the muscle fatigue as the muscle fatigue status.

14. The equipment of claim 13, wherein the extracellular fluid is the ratio of an extracellular fluid to intracellular and extracellular fluids.

15. The equipment of claim 13, wherein the extracellular fluid is an interstitial fluid.

* * * * *